March 3, 1964 E. S. BOERNER Plant Pat. 2,372
CHRYSANTHEMUM PLANT
Filed March 8, 1963
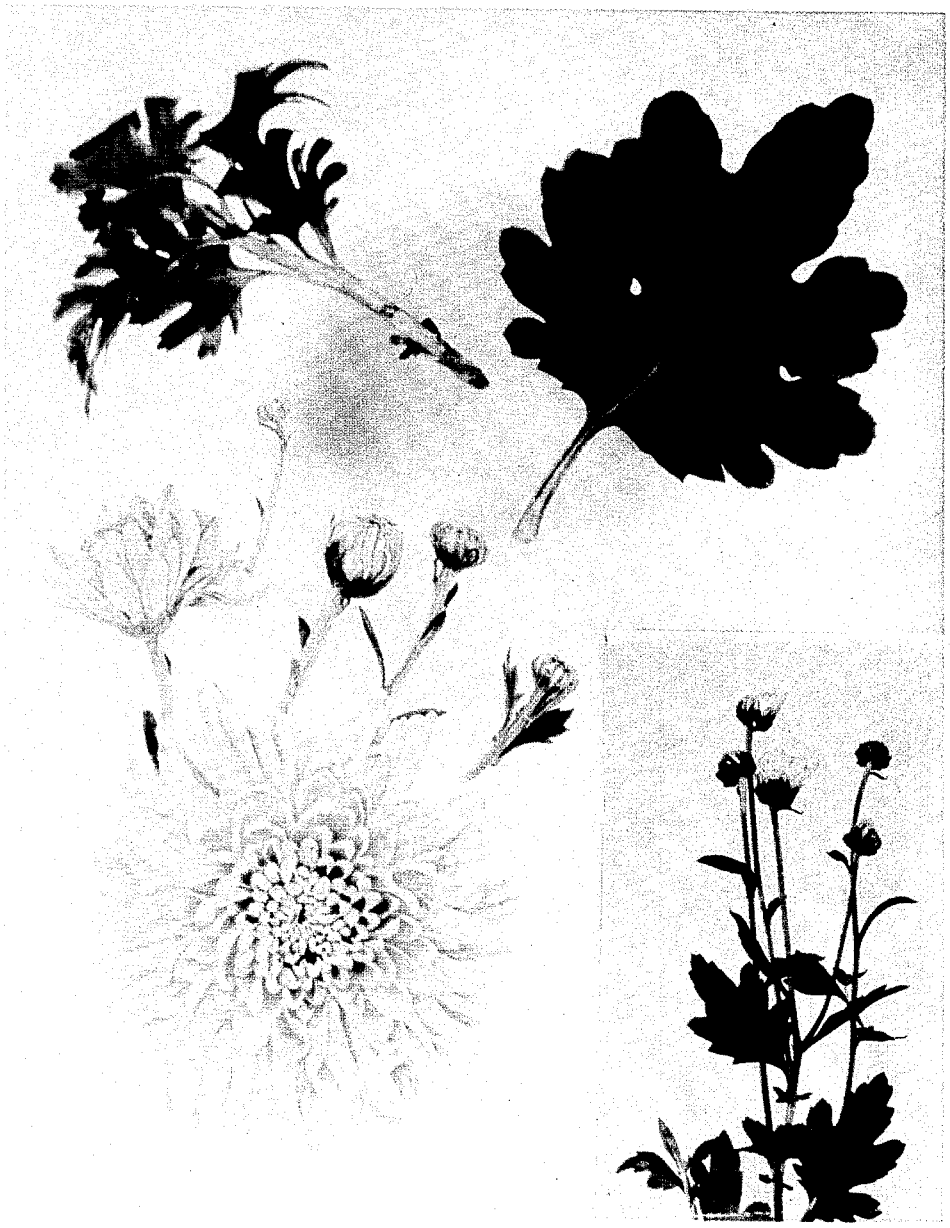
Inventor.
E. S. Boerner
By: Robbins Robb
Attorneys.

United States Patent Office

Plant Pat. 2,372
Patented Mar. 3, 1964

2,372
CHRYSANTHEMUM PLANT

Eugene S. Boerner, Newark, N.Y., assignor to Jackson & Perkins Company, Newark, N.Y., a corporation of New York Filed Mar. 8, 1963, Ser. No. 264,007
1 Claim. (Cl. Plt.—76)

The present invention relates to a new and distinct variety of chrysanthemum plant of the reflex class, which was originated by me by crossing an unnamed and unpatented pink-lavender seedling derived from a cross of "Fred Rockwell" (Plant Patent No. 718) × "Kingbird" (Plant Patent No. 1,306) with an unnamed and unpatented bright orange seedling derived from a cross of "Fred Rockwell" (Plant Patent No. 718) × an unnamed and unpatented large Hortorum seedling.

The primary objective of this breeding was to produce a new chrysanthemum variety having the hardiness and the pink-lavender flower color of the female parent first referred to above, combined with the large flower size of the male parent. This objective was fully achieved, along with other desirable improvements, as evidenced by the following unique combinations of characteristics which are outstanding in the new variety and which distinguish it from its parents, as well as from all other varieties of which I am aware:

(1) Large size of the foliage;

(2) Large flower size, averaging from 5½ inches to 6 inches in diameter;

(3) A thick flower form;

(4) A distinctive and attractive general color tonality of the flowers corresponding to Pale Rosolane Purple, lightly overcast with Liseran Purple, which is an unusual color in chrysanthemum flowers of this size; and (5) Good hardiness.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen plant which is depicted in black-and-white for the purpose of illustrating the form and habit of growth of the plant.

The following is a detailed description of the new variety, with color terminology in accordance with Ridgway's Color Standards and Nomenclature, as based upon observations of specimens grown outdoors at Newark, New York, in the early morning during the latter part of the month of October:

Parentage: Seedling.

*Seed parent.*—An unnamed pink-lavender seedling derived from a cross of "Fred Rockwell" × "Kingbird."

*Pollen parent.*—An unnamed bright orange seedling derived from a cross of "Fred Rockwell" × an unnamed large Horotorum seedling.

Classification: Reflex.

Growth: Upright; strong; vigorous.

Cold resistance: Frost resistant and winter hardy in northern New York State.

Blooming period: From late September until freezing weather.

*Flower*

Bud:

*Color.*—When petals first divide— Light Rosolane Purple, Plate 26. When petals begin to unfurl—Light Rosolane Purple, Plate 26, very lightly overcast with Pale Rosolane Purple, Plate 26. When half-blown: inside—Tyrian Pink, Plate 12, very lightly overcast with Amaranth Pink, Plate 12; outside—Pale Rosolane Purple, Plate 26, very lightly overcast with Light Rosolane Purple, Plate 26.

Peduncle. — Color — Kildare Green, Plate 31. Strength—strong.

Bloom:

*Size.*—From 5½ inches to 6 inches in diameter.

*Stem.*—Strong.

*Form.*—Thick; reflexed.

*Petalage.*—Double.

*Color.*—Center of flower—Amaranth Pink, Plate 12, very lightly overcast with Liseran Purple, Plate 26. Outer petals—Pale Amaranth Pink, Plate 12, lightly overcast with Rose Pink, Plate 12. Base of petals—Light Turtle Green, Plate 32. Inside of petals—Pale Rosolane Purple, Plate 26, lightly overcast with Liseran Purple, Plate 26. Reverse of petals—Rosolane Pink, Plate 26, lightly overcast with Pale Rosolane Purple, Plate 26.

*Petals.*—Texture—thin; crisp. Form—oval.

*Fragrance.*—Characteristic chrysanthemum.

*Plant*

Form: Upright.

Growth: Free; strong.

Foliage:

*Size.*—Large.

*Quantity.*—Normal.

*Color.*—Upper side—Dark Cress Green, Plate 31. Reverse side—Cress Green, Plate 31.

*Texture.*—Leathery.

I claim:

A new and distinct variety of chrysanthemum plant of the reflex class, substantially as herein shown and described, characterized particularly as to novelty by the unique combination of large foliage size, large flower size, thick flower form, a distinctive and attractive general color tonality of the flowers corresponding to Pale Rosolane Purple, lightly overcast with Liseran Purple, and good hardiness.

No references cited.